US012683002B1

(12) United States Patent
Lamoncha

(10) Patent No.: US 12,683,002 B1
(45) Date of Patent: Jul. 14, 2026

(54) PROVIDING EMERGENCY, PREAUTHORIZED ACCESS TO MEDICATION INFORMATION

(71) Applicant: Mark Lamoncha, Columbiana, OH (US)

(72) Inventor: Mark Lamoncha, Columbiana, OH (US)

( * ) Notice: Subject to any disclaimer, the term of this patent is extended or adjusted under 35 U.S.C. 154(b) by 5 days.

(21) Appl. No.: 19/074,830

(22) Filed: Mar. 10, 2025

Related U.S. Application Data

(62) Division of application No. 17/961,163, filed on Oct. 6, 2022, now Pat. No. 12,283,359.

(51) Int. Cl.
| | |
|---|---|
| *G16H 20/13* | (2018.01) |
| *A61B 5/00* | (2006.01) |
| *A61B 5/1172* | (2016.01) |
| *G07C 9/00* | (2020.01) |
| *G07C 9/25* | (2020.01) |
| *G07C 9/27* | (2020.01) |

(Continued)

(52) U.S. Cl.
CPC ........... *G16H 20/13* (2018.01); *A61B 5/1172* (2013.01); *A61B 5/7475* (2013.01); *G07C 9/00563* (2013.01); *G07C 9/00571* (2013.01); *G07C 9/25* (2020.01); *G07C 9/27* (2020.01); *G16H 10/60* (2018.01); *G16H 40/67* (2018.01); *G07C 9/00896* (2013.01); *G07C 2009/0092* (2013.01)

(58) Field of Classification Search
None
See application file for complete search history.

(56) References Cited

U.S. PATENT DOCUMENTS

| | | |
|---|---|---|
| 5,845,255 A | 12/1998 | Mayaud |
| 5,987,519 A | 11/1999 | Peifer et al. |
| 6,523,009 B1 | 2/2003 | Wilkins |

(Continued)

FOREIGN PATENT DOCUMENTS

| | | |
|---|---|---|
| WO | 2017139383 A1 | 8/2017 |

OTHER PUBLICATIONS

Healthit.gov, What is Electronic Prescribing?, https://www.healthit.gov/faq/what-electronic-prescribing, site visited Jul. 31, 2020.

(Continued)

*Primary Examiner* — Fekadeselassie Girma
(74) *Attorney, Agent, or Firm* — Standley Law Group LLP; Jeffrey S. Standley; Adam J. Smith

(57) ABSTRACT

Systems and methods for providing emergency access to information regarding prescribed medications are provide. A request for emergency access is received from a requesting healthcare provider device associated with an emergency provider. The request includes authentication information for a patient received from an authentication device associated with the requesting healthcare provider device. The received authentication information is verified by a server against patient data, including authentication information and medication information for patients, stored at a database. Following successful verification, if the patient data for the patient includes an authorization for emergency access, the database is queried to prescription information associated with the patient, which is transmitted to the requesting healthcare provider device in a read-only format.

20 Claims, 9 Drawing Sheets

(51) Int. Cl.
   *G16H 10/60*     (2018.01)
   *G16H 40/67*     (2018.01)

(56)                    References Cited

U.S. PATENT DOCUMENTS

| | | | |
|---|---|---|---|
| 7,613,620 B2 | 11/2009 | Salwan | |
| 7,769,601 B1 | 8/2010 | Bleser et al. | |
| 8,260,635 B2 * | 9/2012 | Hasan | G16H 50/20 |
| | | | 705/2 |
| 8,335,697 B2 | 12/2012 | Siegel | |
| 8,364,504 B1 | 1/2013 | Bleser et al. | |
| 8,510,131 B1 | 8/2013 | Bleser et al. | |
| 9,129,099 B1 * | 9/2015 | Paruchuri | G06F 21/30 |
| 9,659,269 B2 | 5/2017 | Lamoncha | |
| 10,210,475 B2 * | 2/2019 | Pargoe | G06Q 10/0832 |
| 10,455,354 B2 * | 10/2019 | Hu | H04W 4/02 |
| 10,460,088 B2 * | 10/2019 | Oka | H04N 23/00 |
| 10,614,914 B2 * | 4/2020 | Gondek | G16H 10/60 |
| 10,959,058 B1 * | 3/2021 | Stark | H04W 4/029 |
| 11,556,887 B2 | 1/2023 | Pargoe | |
| 11,738,883 B2 * | 8/2023 | O'Toole | A47G 29/141 |
| | | | 340/946 |
| 11,790,309 B1 * | 10/2023 | Wahba | G07C 9/00309 |
| | | | 705/332 |
| 12,039,483 B2 * | 7/2024 | Blake | G06Q 10/083 |
| 2002/0035484 A1 | 3/2002 | Mccormick | |
| 2002/0111829 A1 | 8/2002 | Robibero | |
| 2002/0143434 A1 | 10/2002 | Greeven et al. | |
| 2003/0050802 A1 | 3/2003 | Jay et al. | |
| 2004/0006490 A1 | 1/2004 | Gingrich et al. | |
| 2004/0225527 A1 | 11/2004 | Holz | |
| 2004/0225528 A1 | 11/2004 | Brock | |
| 2005/0182656 A1 | 8/2005 | Morey | |
| 2005/0281601 A1 | 12/2005 | Papetti | |
| 2006/0031094 A1 | 2/2006 | Cohen et al. | |
| 2006/0041330 A1 | 2/2006 | Ansari et al. | |
| 2006/0064326 A1 | 3/2006 | Tucker | |
| 2006/0076420 A1 * | 4/2006 | Prevost | G06Q 20/3552 |
| | | | 235/492 |
| 2008/0042423 A1 | 2/2008 | Roberts et al. | |
| 2008/0071572 A1 | 3/2008 | Ahmed | |
| 2009/0106313 A1 | 4/2009 | Boldyga | |
| 2010/0181374 A1 | 7/2010 | Martis et al. | |
| 2010/0228968 A1 * | 9/2010 | Wason | H04L 9/3263 |
| | | | 713/169 |
| 2013/0173280 A1 | 7/2013 | Denny | |
| 2014/0032034 A1 | 1/2014 | Raptopoulos et al. | |
| 2014/0254896 A1 | 9/2014 | Zhou et al. | |
| 2015/0120094 A1 | 4/2015 | Kimchi et al. | |
| 2017/0147783 A1 | 5/2017 | Carroll | |
| 2018/0105289 A1 * | 4/2018 | Walsh | A47G 29/141 |
| 2021/0172930 A1 * | 6/2021 | Pamula | A61M 1/0259 |
| 2021/0358605 A1 * | 11/2021 | Lamoncha | G06Q 20/065 |
| 2022/0119105 A1 * | 4/2022 | Schmalzried | B64U 10/20 |
| 2022/0404839 A1 * | 12/2022 | Tzukerman | G05D 1/0684 |
| 2023/0112944 A1 * | 4/2023 | Pargoe | B64C 39/024 |
| | | | 232/38 |
| 2023/0343159 A1 * | 10/2023 | Poddar | G16H 20/13 |
| 2023/0360455 A1 * | 11/2023 | Poddar | G07C 9/00563 |
| 2023/0410028 A1 * | 12/2023 | O'Toole | B64D 47/02 |
| 2024/0076129 A1 * | 3/2024 | Stark | B65G 1/1371 |

OTHER PUBLICATIONS

American Psychiatric Association, e-Prescribing (eRX), https://www.psychiatry.org/psychiatrists/practice/practice-management/health-information-technology/e-prescribing, site visited Jul. 30, 2020.

Centers for Disease Control and Prevention, Prescription Drug Monitoring Programs (PDMPs), https://www.cdc.gov/drugoverdose/pdmp/states.html, site visited Jul. 30, 2020.

Youdelman, M. et al., Language Services Resource Guide for Pharmacists, Feb. 2010, The National Health Law Program.

Mills et al., Unique health identifiers for universal health coverage, article, published Oct. 17, 2019, 8 pages.

* cited by examiner

1/9

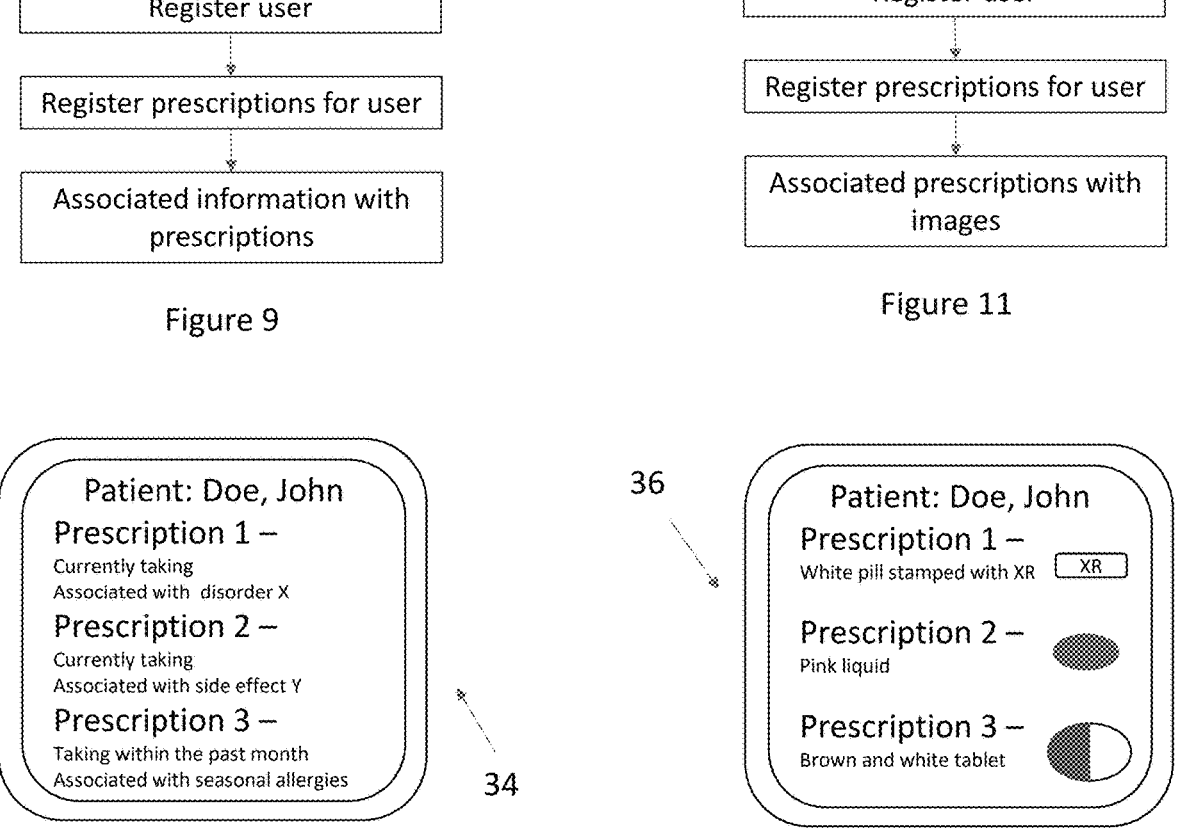

Register user

Register prescriptions for user

Associated information with prescriptions

Figure 9

Register user

Register prescriptions for user

Associated prescriptions with images

Figure 11

Patient: Doe, John

Prescription 1 –
Currently taking
Associated with disorder X

Prescription 2 –
Currently taking
Associated with side effect Y

Prescription 3 –
Taking within the past month
Associated with seasonal allergies

Patient: Doe, John

Prescription 1 –
White pill stamped with XR    XR

Prescription 2 –
Pink liquid

Prescription 3 –
Brown and white tablet

Figure 12

PROVIDING EMERGENCY, PREAUTHORIZED ACCESS TO MEDICATION INFORMATION

CROSS-REFERENCE TO RELATED APPLICATIONS

This application is a divisional of U.S. application Ser. No. 17/961,163 filed Oct. 6, 2022, the disclosures of which are hereby incorporated by reference as if fully restated herein.

TECHNICAL FIELD

Exemplary embodiments relate generally to systems and methods for providing emergency, preauthorized access to medication information.

BACKGROUND AND SUMMARY OF THE INVENTION

Accessibility to prescribed medications is difficult to obtain when traveling. For example, one might leave for a trip and forget to pack their medication, have their prescription stolen, lose their prescription, or not realize that they only have a two-day supply left in their current prescription, but they are scheduled to be gone for a week. In such cases and others, it may be difficult to obtain needed medications. Even where a prescription is available (new, refill, or the like), it may not be desirable to fully transfer a prescription to another pharmacy. In some cases, the transfer may take several days. For example, transferring pharmacies sometimes have little motivation to move a prescription from their business such that transfers are a low priority item. Indeed, in some cases no refills are even left for a pharmacy to act on. Getting in contact with the prescribing physician to have a new prescription issued at a new pharmacy is time consuming and may then require later transferring the new prescription back to the original pharmacy. This difficulty is sometimes compounded by the fact that access to the medication may be critical to ensuring appropriate care and continued health. As another example, an ongoing global pandemic may leave a patient stranded in a remote location or otherwise render an in-person consultation less than desirable. In such cases, a prescription (new, refill, or the like) may be difficult or impossible to otherwise obtain.

Even where a refill may be available, obtaining the refilled prescription may be difficult. For example, when traveling, individuals may not be familiar with local resources and may be unconformable with wayfinding. Traveling or not, individuals may have limited mobility or limited access to transportation. As another example, on ongoing global pandemic may leave a patient under temporary quarantine or unable to safely travel publicly. Traditional mail or parcel services may take several days to complete shipping, and thus may be inadequate to meet a patient's immediate needs.

Systems and methods for providing global accessibility prescribed medications are disclosed herein. The discloses systems and methods may include secure, automated delivery options.

A new prescription, a prescription refill, a prescription modification, and/or other prescription information may be received at one or more remote servers. A database, preferably cloud-based, may be updated with the prescription information. The prescription information may be stored in association with patient data. The database may comprise a single or multiple databases. The database may be for geographically disburse patients, such as across state and/or country lines. The database may include location, medication availability, and/or pricing information for pharmacies.

Patient data, such as a patient identifier (e.g., user name, password, keycode, PIN, name, address, unique identifier, birthdate, phone number, social security number (or part of), driver's license number, passport number, national identification number, authentication information (biometric, passcodes, etc.), combinations thereof, or the like), may be received and verified. Prescriptions associated with the patient may be queried from the database and transmitted to a requesting user device. Data may be included with such transmissions including nearby pharmacies, availability of medication information, delivery options, pricing, and the like.

A user selection of one of the transmitted prescriptions may be received, such as at the one or more servers, and the database updated accordingly to reflect the dispensing of the prescription. Payment may be processed, such as by way of the payment module 46. Payment may be processed before or after scheduling and/or performing delivery, patient pick up, combinations thereof, or the like. Delivery may be scheduled and performed, such as by way of one or more autonomous drones, which may be capable of flight. The drones may be configured to carry one or more locking containers for the prescribed medication. In exemplary embodiments, without limitation, the drones may be programmed with delivery location information and the containers may be programmed with authentication information.

Upon delivery, authentication information may be received and verified. Upon verification, a compartment of a container carrying the medication may be unlocked to permit access to the medication. In exemplary embodiments, without limitation, the authentication information may be locally verified at the container. The disclosed systems and methods permit prescriptions to be quickly and securely dispensed and delivered, such as in an at least partially automated fashion. Alternatively, or additionally, the disclosed systems and methods may be utilized for delivery to pharmacies, healthcare providers, or the like for subsequent administration, dispensing, or the like the patients by the disclosed systems and methods or traditional routes.

Further features and advantages of the systems and methods disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 9 is a flow chart with exemplary logic for operating the system of FIG. 1 to provide medication information;

FIG. 10 is a plan view of an exemplary display for the medication information of FIG. 9;

FIG. 11 is a flow chart with exemplary logic for operating the system of FIG. 1 to provide medication identification;

FIG. 12 is a plan view of an exemplary display for the medication identification feature of FIG. 11.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
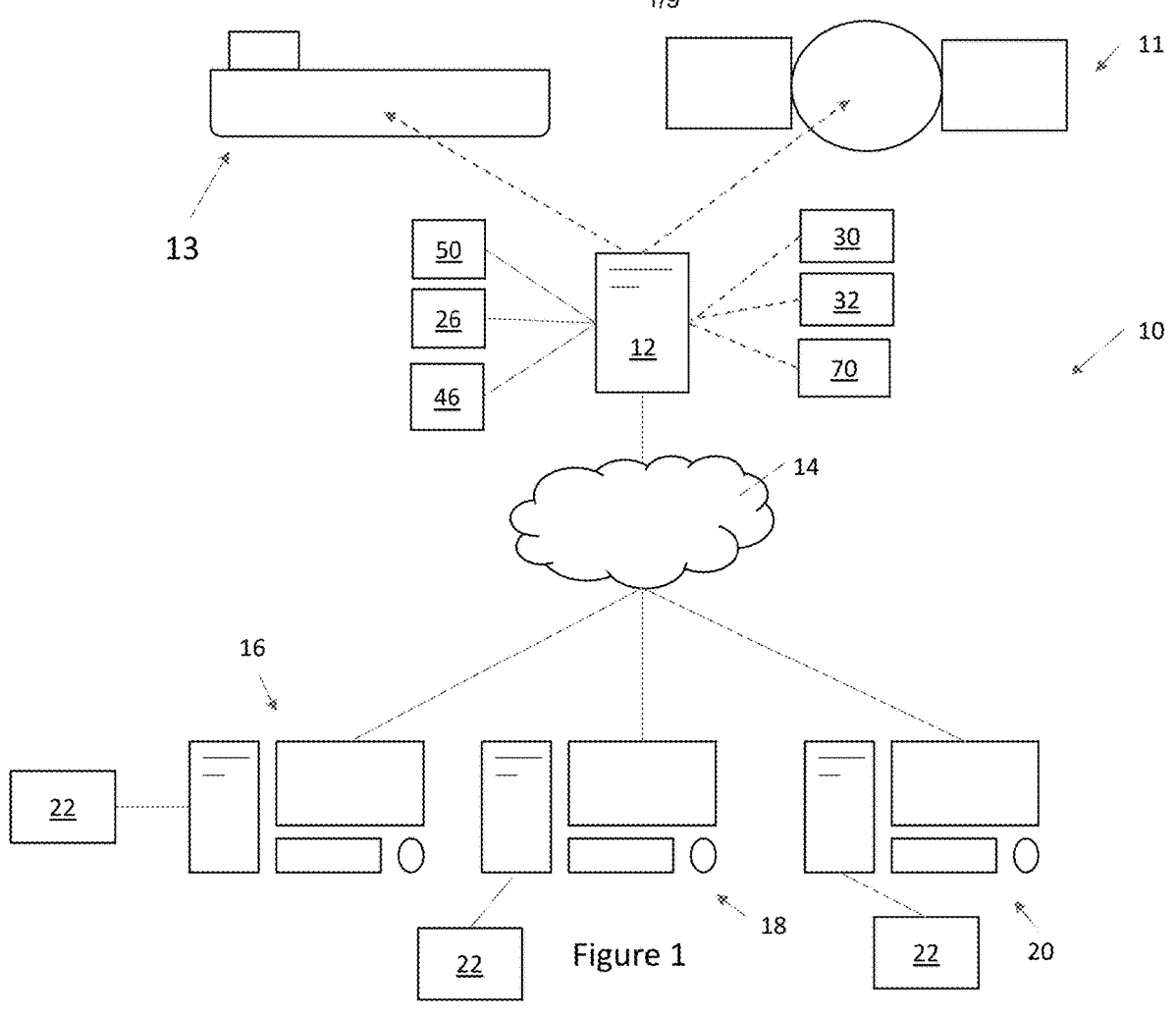
FIG. 1 is a plan view of an exemplary prescription system.

FIG. 1 is a plan view of an exemplary system 10. The system 10 may comprise a patient prescription database subsystem 12 (hereinafter also the "prescription database"). The patient prescription database subsystem 12 may be in electronic communication with one or more pharmacy systems 16. The patient prescription database subsystem 12 may be in electronic communication with one or more patient systems 18. The patient prescription database subsystem 12 may be in electronic communication with one or more healthcare provider systems 20. Such electronic communication may be made by way of one or more networks 14.

The patient prescription database subsystem 12 may comprise one or more databases, servers, processors, electronic storage devices, combinations thereof, or the like. The patient prescription database subsystem 12 may, alternatively or additionally, comprise one or more cloud-based storage systems. The patient prescription database subsystem 12 may comprise one or more devices housed at a single location or distributed amongst multiple locations. The patient prescription database subsystem 12 may include patient information from pharmacies 60, patients, and/or healthcare providers in various geographic areas, such as different states, countries, regions, towns, continents, combinations thereof, or the like.

Each pharmacy system 16 may be associated with one or more pharmacists, pharmacies 60, some combination thereof, or the like. Each pharmacy system 16 may comprise one or more electronic devices such as, but not limited to, personal computers, laptops, tablet computers, smartphones, smartwatches, servers, processors, electronic storage devices, some combination thereof, or the like. Each pharmacy system 16 may comprise software programs for tracking prescription and dispensing or other medical information for patients. Each pharmacy system 16 may comprise the same or different components.

Each patient system 18 may be associated with one or more patients and may comprise one or more electronic devices such as, but not limited to, personal computers, laptops, tablet computers, smartphones, smartwatches, servers, processors, electronic storage devices, some combination thereof, or the like. Each patient system 18 may comprise the same or different components.

Each healthcare provider system 20 may be associated with one or more healthcare providers, offices, some combination thereof, or the like. Each healthcare provider system 20 may comprise one or more electronic devices such as, but not limited to, personal computers, laptops, tablet computers, smartphones, smartwatches, servers, processors, electronic storage devices, some combination thereof, or the like. Each healthcare provider system 20 may comprise software programs for tracking diagnoses, prescribing medications, tracking medications, and/or other medical information for patients. For example, without limitation, the healthcare provider systems 20 may comprise electronic medical record ("EMR") systems, electronic health record ("EHR") systems, personal electronic devices, combinations thereof, or the like. Each healthcare provider system 20 may comprise the same or different components.

The network(s) 14 may comprise one or more internets, intranets, the world wide web, cellular networks, wired networks, wireless networks, LANs, some combination thereof, or the like. The networks 14 may comprise wired and/or wireless connections.

The system 10 may include a blockchain module 50, though such is not required. Additions, deletions, and/or other revisions to the patient prescription database subsystem 12 may be provided by way of one or more blockchains. Blocks may be issued by the blockchain module 50 accordingly. For example, adding new prescriptions, expiration of prescriptions, dispensation of full or partial refills, new patients, authentication information, modifications or other updates to any of the foregoing, combinations thereof, or the like may all be tracked by issuing blocks to the blockchains by way of the blockchain module 50. In exemplary embodiments, without limitation, each block of the blockchain includes payment and other transaction information (e.g., prescription information).

One or more of the pharmacy systems 16, the patient systems 18, and/or the healthcare provider system 20 may comprise one or more authentication devices 22. The authentication devices 22 may comprise fingerprint readers, palm scanners, iris scanners, facial recognition devices, voice recognition devices, software, combinations thereof, or the like. The authentication devices 22 may be part of the pharmacy systems 16, the patient systems 18, and/or the healthcare provider system 20 or separate therefrom. For example, without limitation, the authentication devices 22 may utilize or comprise cameras, touchscreens, biometric readers, combinations thereof, or the like which are provided at the pharmacy systems 16, the patient systems 18, and/or the healthcare provider system 20 to also perform other functionality. For example, without limitation, the authentication devices 22 may comprise or utilize a touchscreen of a smartphone to capture fingerprint information, a camera of a smartphone to capture facial recognition data, combinations thereof, or the like. Any type, kind, and/or number of authentication devices 22 may be utilized. The authentication devices 22 and/or related components may comprise those available from Integrated Biometrics, LLC of Spartanburg, South Carolina (integratedbiometrics.com), including but not limited to the SLAPSHOT product(s), by way of non-limiting example. Alternatively, or additionally, the authentication devices 22 may comprise keyboards, keypads, card readers, near field communication devices, combinations thereof, or the like configured to receive information such as, but not limited to, user names, passwords, key codes, one time access codes, combinations thereof, or the like.

The system 10, and/or various components thereof, may be positioned in one or more orbital systems 11. The orbital systems 11 may comprise, for example without limitation, satellites, space stations, ships, orbiting platforms, high altitude balloons, dirigibles, combinations thereof, or the like. The orbital systems 11 may be configured for single or regular travel at or above the Karman line by way of non-limiting example. Alternatively, or additionally, the system 10, and/or various components thereof, may be positioned in one or more offshore locations 13. The offshore locations 13 may comprise, for example without limitation, ships or other oceangoing vessels, offshore platforms, submersibles oil rigs, combinations thereof, or the like. The offshore locations 13 may be configured for single or regular travel in international waters. In exemplary embodiments, without limitation, the patient prescription database subsystem 12, or components thereof, such as but not limited to the server(s) and/or database(s) may be placed in the orbital systems 11 and/or offshore locations 13. In this fashion, the system 10, and/or various components thereof, may be maintained in international jurisdictions (e.g., international waters). Patient addresses may be recorded, such as at the patient prescription database subsystem 12, at one or more of the orbital systems 11 and/or offshore locations 13.

Portions of the patient prescription database subsystem 12 may be geographically disbursed. For example, without limitation, some of the patient prescription database subsystem 12, or components thereof, may be placed in orbital systems 11 and/or offshore locations 13 while others are provided at one or more land-based geographic locations.

The patient prescription database subsystem 12 may comprise, or be in electronic communication with, a delivery subsystem 70. In exemplary embodiments, without limitation, some or all of the delivery subsystem 70 may be provided at one or more land-based geographic locations.

The patient prescription database subsystem 12 may comprise, or be in electronic communication with, a telehealth subsystem 30.

The patient prescription database subsystem 12 may comprise, or be in electronic communication with, a payment module 46. The payment module 46 may be configured to automatically generate and transmit requests for reimbursement to insurance providers, generate and transmit invoices to the patient, electronically process payments, electronically disburse payments to providers and/or pharmacies 60, electronically collect payment from patients, some combination thereof, or the like.

The payment module 46 may be configured to accept and/or generate one or more cryptocurrencies. Such cryptocurrencies may include, for example without limitation, those currently known and/or one or more newly developed currencies. Such cryptocurrencies and/or transaction information related to the same may be stored at one or more blockchains, such as part of one or more distributed ledgers. The cryptocurrencies may comprise one or more coins or blocks. Each coin or block may comprise data indicating a particular prescription, patient, prescription transaction information, patient information, pharmacy information, healthcare provider information, delivery information, combinations thereof, or the like, as well as serve as financial payment for the underlying medication or transaction. For example, without limitation, each coin or block may comprise a unique identifier for a prescription and/or prescription transaction (e.g., dispensing or part or full prescription), number of refills available, expiration of prescription, combinations thereof, or the like. Alternatively, or additionally, each coin or block may comprise one or more indicators of value (e.g., denomination). In this fashion, the patient prescription database subsystem 12 may permit exchange of prescription information and payment in a single transaction.

The payment module 46 may be configured to automatically and electronically exchange currencies. For example, without limitation, the payment module 46 may be configured to automatically and electronically exchange foreign currencies, cryptocurrencies (such as by way of one or more online exchange marketplaces), combinations thereof, or the like. The payment module 46 may be configured to automatically and electronically interact with various banking and/or brokerage systems. In this fashion, payments may be collected and disbursed to various accounts, such as those associated with patients, users, pharmacies, healthcare providers, system administrators, insurance providers, payors, payment processors, combinations thereof, or the like. For example, without limitation, insurance payment, co-payment, and the like may be administered (e.g., determined, collected, and/or disbursed) through the patient prescription database subsystem 12, such as by way of the payment module 46. Payment may be automatically provided in the denomination specified by the user, pharmacy 60, insurance provider, or the like (e.g., locally accepted currency and/or preferred currency). The payment module 46 may be configured to automatically and electronically process credit card, debit card, electronic check, cryptocurrency, and/or banking information by way of non-limiting example. The payment module 46 may be configured to automatically and electronically process payments at any time, such as before or at the time of dispensing.

The patient prescription database subsystem 12 may comprise, or be in electronic communication with, an availability module 26. The availability module 26 and/or one or more databases of the patient prescription database subsystem 12 may comprise data regarding pharmacies 60, such as but not limited to, location information, operating hours information, contact information, availability of stock information, accepting insurance information, delivery options information, pricing information, combinations thereof, or the like. Such information may be regularly updated, such as by way of the pharmacy systems 16.

In exemplary embodiments, without limitation, prescription information, patient data, and/or other data related to each respective patient may reside within the patient prescription database 12 in a respective electronically partitioned area. The patient prescription database 12 may be the only database that the prescriptions reside on during their existence, though such is not required. The patient prescription database 12 may be electronically partitioned so as to provide a private, virtual storage vault for the patient's prescription(s) or other information. For example, each patient's prescription(s) may be contained with a partitioned area of the patient prescription database 12 such that the area is not shared with any other patients. In exemplary embodiments, the prescribing healthcare provider may upload a prescription directly to the patient's partitioned area within the database 12 and the prescription may be removed once dispensed or expired. The data residing within a given one of the partitioned areas, in exemplary embodiments, may only be viewed and/or modified upon dual verification such as, but not limited to, by way of entry and verification of a unique patient identifier and one or more of: a unique healthcare provider identifier, a unique pharmacist identifier, and a unique administrator identifier.

The patient prescription database 12 may comprise, or be in electronic communication with, one or more medication information databases 32. The medication information databases 32 may comprise information about medications including, for example without limitation, images of medications, description information for medications, contraindication information for medications, side effect information, combinations thereof, or the like. Information in the medication information databases 32 may be provided or derived from one or more public and/or private sources.

Figure 2:
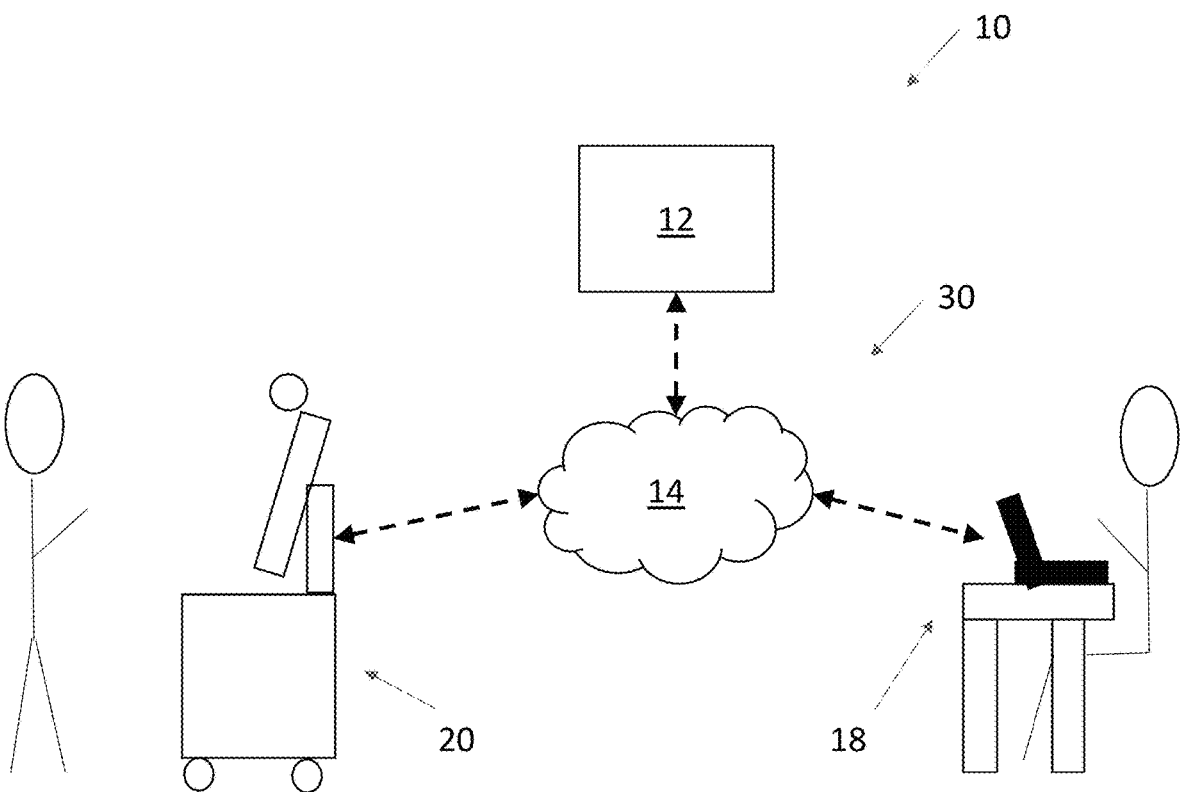
FIG. 2 is a plan view of an exemplary telehealth subsystem for use with the system of FIG. 1.

FIG. 2 illustrates the telehealth subsystem 30. The healthcare provider system 20 may comprise certain telehealth features, subsystems, and/or components such as, but not limited to, telephones, text messaging systems, email systems, VOIP systems, web cams, cameras, video conferencing systems, microphones, speakers, electronic displays, computers, tablets, smartphones, some combination thereof, or the like. The patient system 18 may comprise certain telehealth features, subsystems and/or components such as, but not limited to, telephones, text messaging systems, email systems, VOIP systems, web cams, cameras, video conferencing systems, microphones, speakers, electronic displays, computers, tablets, smartphones, some combination thereof, or the like. Electronic communication may be established between the patient and the healthcare provider by way of one or more networks 14.

The telehealth consultation may be arranged and/or provided by way of the telehealth subsystem 30, though such is not required. The telehealth consultation may comprise audio and/or video components. The telehealth consultation may result in the prescription of one or more medications by way of a new prescription, a refill, some combination thereof, or the like.

Before, during, or after the telehealth consultation, evidence may be presented to and/or gathered by the healthcare provider. In exemplary embodiments, the evidence may comprise one or more images, videos, or the like of an injury or other condition. Alternatively, or additionally, the evidence may comprise test results, medical imaging results, self-reported symptoms, some combination thereof, or the like. The evidence may be related to the symptoms, diseases, conditions, or the like related to the prescription of medications.

The evidence may be uploaded to the patient prescription database subsystem 12. In exemplary embodiments, the evidence may be uploaded to the same electronically partitioned area as the associate prescription(s). The evidence may remain in the electronically partitioned area for the same time as the associate prescription(s), though such is not required. For example, without limitation, the evidence may remain in the patient prescription database subsystem 12 for a longer period of time or indefinitely.

Before or after upload, the evidence may be associated with one or more prescriptions prescribed, refilled, or the like by the healthcare provider in conjunction with the consultation. The evidence may be retrieved from the patient prescription database subsystem 12 in conjunction with the retrieval of prescriptions as detailed herein.

The evidence may be retrieved when the prescription is accessed to verify the patient's identity. Alternatively, or additionally, the evidence may be accessed to compare a patient's current presentation with a former presentation for purposes of evaluating the adequacy of a prescription, the potential for fraud, mistake, and/or misunderstanding, the need for a refill, the need for further treatment, some combination thereof, or the like.

For example, without limitation, the patient may present with an ongoing skin condition. A picture of the skin condition may be uploaded as evidence with the prescription. The dispensing pharmacy may access the evidence to verify that the person to whom the pharmacy is dispensing the medication is indeed the patient. Alternatively, or additionally, the healthcare provider may access the evidence to compare the evidence against the patient's current symptoms to see if a refill, a different dose, an alternative medication, or the like are warranted. Alternatively, or additionally, the healthcare provider or another party may access the evidence to verify cause for prescribing and dispensing the medication.

As another example, without limitation, if the evidence associated with a narcotics prescription shows significant bruising around the midsection, but the party asserting themselves to be the patient for dispensation of the medication shows no such bruising a determination may be made that the prescription was obtained fraudulently, is no longer needed, some combination thereof, or the like. As another example, again without limitation, evidence of the same injury may be provided for multiple prescription for narcotics from multiple healthcare providers, tending to indicate fraud. Upon review of such multiple prescriptions for narcotics for the same injury, the healthcare provider and/or the pharmacist may determine that fraud may be occurring.

The patient prescription database subsystem 12 may be contained within a single electronic storage device or spread across multiple, locally or remotely located electronic storage devices.

Figure 3:
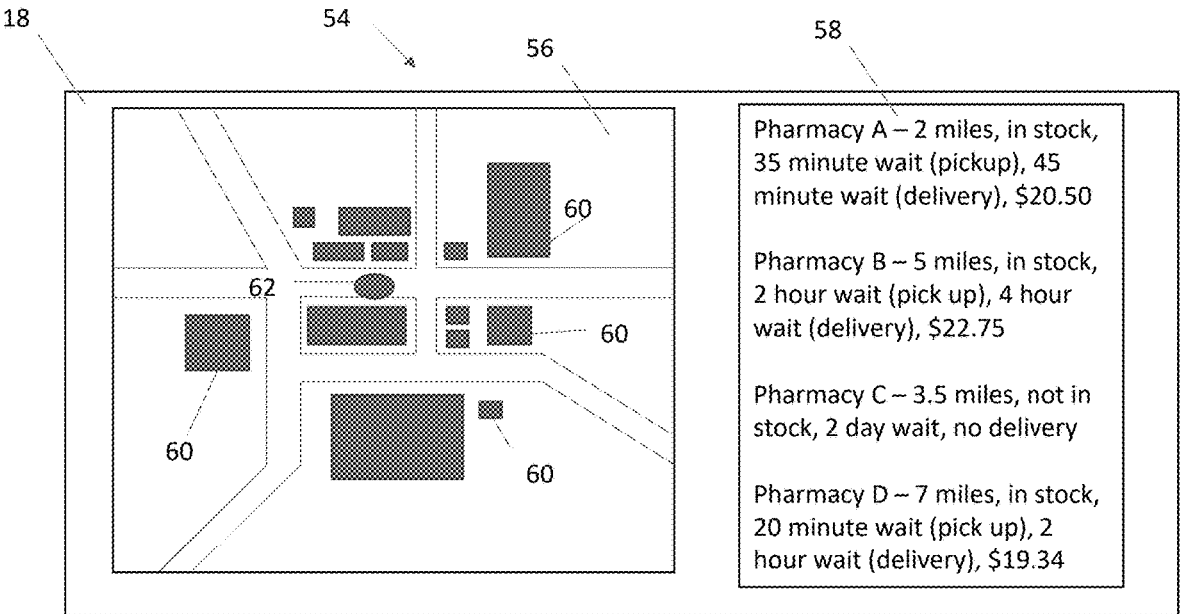
FIG. 3 is an exemplary pharmacy selection user interface for use with the system of FIG. 1.

FIG. 3 is an exemplary user interface 54 for selecting a dispensing pharmacy 60. The user interface 54 may be generated, in whole or in part, by the patient prescription database subsystem 12, such as by way of the availability module 26.

Pharmacies 60 associated with pharmacy systems 16 in communication with the patient prescription database subsystem 12 may be identified. Such identification may be made by way of the availability model 26 and/or upon receipt of a user selection of a prescription for dispensing, in exemplary embodiments without limitation. In exemplary embodiments, pharmacies 60 within a predetermined or variable geographic distance from a location 62 of the patient system 18 and or another location 62 specified at the patient system 18 may be identified. The location maybe automatically detected by the patient system 18, manually entered at the patient system 18, and/or based on stored patient data.

Such pharmacies 60 may be shown on a map 56 in their approximate geographic location. The location 62 may also be shown on the map 56. The location may be determined by a location device at the patient system 18, manual entry, preprogramming, some combination thereof, or the like.

The user interface 54 may comprise pricing information, which may be generated electronically and/or provided by the pharmacies 60 and/or pharmacy systems 16, such as by way of the availability module 26.

A listing of the pharmacies 60 may be generated at the same or a different screen 58. The listing may identify each of the pharmacies 60, their approximate geographic distance from the location 62, the availability of one or more prescriptions associated with the patient, and the approximate wait time for pick up and/or delivery (if available). The location of the pharmacy 60, and therefore the distance from the location specified by the patient system 18, may be determined by determined by a location device at the pharmacy system 16, manual entry, preprogramming, some combination thereof, or the like. In exemplary embodiments, the time for a prescription to be filled and/or delivered may be determined, at least in part, by the systems shown and described in U.S. Pat. No. 9,659,269 issued May 23, 2017, the disclosures of which are hereby incorporated by reference as if fully restated herein.

Some or all of the information shown and/or described may be provided by the by way of the availability module 26, though such is not required.

The illustrated embodiment is merely exemplary and not intended to be limiting. Other types or forms of information may be presented.

Figure 4:
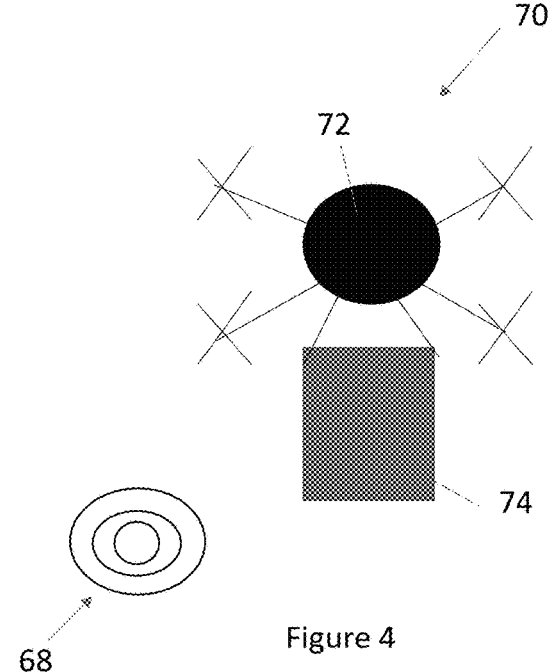
FIG. 4 is an exemplary autonomous delivery subsystem for use with the system of FIG. 1.

FIG. 4 illustrates an exemplary autonomous delivery subsystem 70, such as for use with the system 10. The autonomous delivery subsystem 70 may comprise, and/or be configured to interact with, one or more drones 72.

The drone(s) 72 may be configured for air flight, though such is not necessarily required. The drone(s) 72 may be configured for manually piloting, such as by way of wireless connection, and/or may be configured for fully or partially automated travel. Alternatively, or additionally, the autonomous delivery subsystem 70 may comprise other types or kinds of fully or partially automated drones 72, such as but not limited to, wheeled vehicles, tracked vehicles, walking vehicles, humanoid robots, boats, submersibles, lighter-than-air transportation vehicles, automobiles, scooters, combinations thereof, or the like configured for ground travel, water travel, air travel, combinations thereof, or the like. The drone 72 may be any type or kind of commercially available vehicle. An example, without limitation, of such a drone 72 capable of flight is the MATRICE 600PRO from SZ DJI Technology Co., Ltd. of Los Angeles, CA (www.dji.com). Any type or kind or drones 72 of the same or different type may be utilized. The illustrated drone 72 is provided by way of example and is not intended to be limiting.

The autonomous delivery subsystem 70 may comprise one or more containers 74. The drones 72 may be configured to removably accept the containers 74, such as by way of one or more brackets, grippers, suction devices, magnets, platforms, holders, clips, fasteners, combinations thereof, or the like. The containers 74 may be provided in various sizes, shapes, or types. Each of the drones 72 may be configured to accept a single or multiple containers 74 of a same or different type.

The drones 72 may comprise one or more wayfinding devices, such as but not limited to, compasses, location tracking devices, cameras and image recognition software, combinations thereof, or the like. In exemplary embodiments, without limitation, the drones 72 may be configured to detect wireless signals, such as but not limited to near field communication signals provided by the pharmacy system 16, the patient systems 18, and/or the healthcare provider system 20. Such electronic communication signals may be specified by the patient prescription database subsystem 12, though such is not required.

Alternatively, or additionally, the drones 72 may be configured to optically detect one or more targets 68 presented, such as by electronic display at or by the pharmacy system 16, the patient systems 18, and/or the healthcare provider system 20, printed and manually displayed, or otherwise provided and manually displayed. Such targets 68 may be specified by the patient prescription database subsystem 12, though such is not required, the targets may comprise, for example without limitation, QR codes, barcodes, electronically scannable codes, wireless beacons, near field communications devices, lights (visible or otherwise), patterns, combinations thereof, or the like. Alternatively, or additionally, the drones 72 may be configured to travel to particular geographic coordinates specified and programmed at the patient prescription database subsystem 12, for example without limitation. In exemplary embodiments, without limitation, the drones 72 may be configured for travel near a specified delivery location, and final delivery area may be placed at the provided target 68. Alternatively, or additionally the drones 72 may be configured to automatically identify acceptable placement locations, such as but not limited to by image recognition software (e.g., door, rooftop, porch, etc.).

In exemplary embodiments, without limitation, the drones 72 may be configured to prevent landing or otherwise stopping more than a predetermined distance (e.g., 100 feet) from a delivery address. For example, without limitation, if a target 68 is positioned more than the predetermined distance from the delivery address programmed, the drone 72 may refuse to land at the target 68. In exemplary embodiments, without limitation, remote authentication, such as by one or more user smart devices, may be provided to permit programming of an alternate delivery address, and/or specific landing or final destination outside of the predetermined distance. This may assist with preventing mis-deliveries or fraud. The user may be able to specify the presence or non-presence of a target 68, such as by way one or more smart user devices, user preferences, combinations thereof, or the like.

Figure 5:
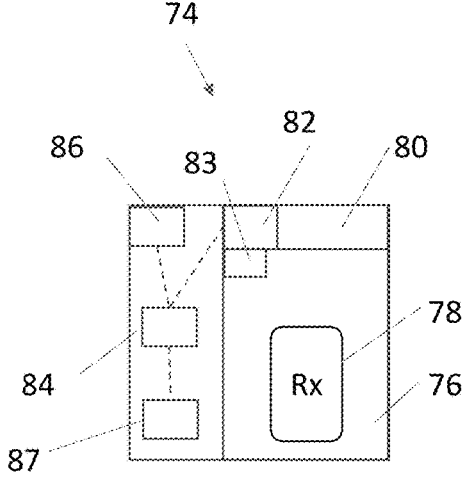
FIG. 5 is a side sectional view of an exemplary delivery container for use with the system of FIG. 1.

FIG. 5 illustrates an exemplary container 74. The container 74 may comprise a compartment 76. The compartment 76 may be accessible by way of an access panel 80. The access panel 80 may comprise a door, lid, sliding panel, combinations thereof, or the like. The access panel 80 may be configured for movement between a closed position where an interior of the compartment 76 is inaccessible and an opened position whereby the interior of the compartment 76 is accessible. The compartment 76 may be sized or otherwise configured to hold one or more medications and/or prescription container for medications 78 (e.g., vials, syringes, pill containers, bottles, combinations thereof, or the like).

The container 74 may comprise one or more thermal management devices 86, such as for maintaining temperature or other environment characteristics of the compartment(s) 76. The thermal management devices 86 may include, for example without limitation, thermoelectric modules, heaters, heat exchangers, heat pipes, fans, ice packs, refrigerants, heating packs, humidifiers, dehumidifiers, desiccants, combinations thereof, or the like. The container 74 may comprise one or more insulating materials. The container 74 may comprise one or more walls comprised of metal or metal alloy (e.g., titanium). The container 74 may comprise one or more shock absorbing materials, such as rubber by way of non-limiting example.

The container 74 may comprise one or more locking devices 82. The locking devices 82 may be configured to selectively secure the access panels 80. The locking devices 82 may be movable between a locked position, whereby the access panel 80 is secured in a locked position, and an unlocked position, whereby the access panel 80 may be opened. The locking devices 82 may be manually and/or automatically operable. In exemplary embodiments, without limitation, the locking device 82 is configured for automatic operation and the locking device 82 comprises a manual override option, and/or a secondary, override manual locking device 82 is provided. Where multiple compartments 76 are provided, each may comprise one or more of the access panels 80 and the locking devices 82. The locking devices 82 may comprise bars, combination dials, cams, gears, motors, actuators, slots, linkages, latches, key hole, key, combination dial, keypad, near field communication device, combinations hereof, or the like. Any type or kind of manual and/or automatic locking device(s) 82 may be utilized.

The container 74 may comprise one or more authentication devices 86. The authentication devices 86 may comprise fingerprint readers, palm scanners, iris scanners, facial recognition devices, voice recognition devices, software, combinations thereof, or the like. The authentication devices 86 may be part of the container 74 or separate therefrom. Any type, kind, and/or number of authentication devices 86 may be utilized. The authentication devices 86 and/or related components may comprise those available from Integrated Biometrics, LLC of Spartanburg, South Carolina (integratedbiometrics.com), including but not limited to the SLAPSHOT product(s), by way of non-limiting example. Alternatively, or additionally, the authentication devices 86 may comprise keyboards, keypads, card readers, near field communication devices, combinations thereof, or the like configured to receive information such as, but not limited to, user names, passwords, key codes, one time access codes, combinations thereof, or the like.

The container 74 may comprise one or more controllers 84. The controllers 84 may each comprise one or more processors and/or one or more electronic storage devices. The controller(s) 84 may be electronic communication with, or integrated with, the authentication device(s) 86, the locking device(s) 82, the access panel(s) 80, the thermal management device(s) 86, combinations thereof, or the like. The controllers 84 may be configured to operate the authentication device(s) 86, the locking device(s) 82, the access panel(s) 80, the thermal management device(s) 86, combinations thereof, or the like.

The container 74 may be locally operated by the controller 84. In this fashion, the container 74 may be otherwise inaccessible, such as to improve privacy and/or security. The controller 84 and/or the container 74 may, alternatively or additionally, be remotely operated, such as by way of the patient prescription database subsystem 12. Communications may be provided by way of one or more wireless networks and may be encrypted or otherwise secured.

Alternatively, or additionally, the containers 74 may comprise one or more tamper resistance devices 83. The tamper resistance devices 83 may be mechanically connected to the access panels 80 and/or the locking devices 82, or components thereof. The tamper resistance devices 83 may be in electronic communication with the controllers 84, though such is not required. The tamper resistance devices 83 may be configured for automatic activation upon forced entry into the container 74. For example, without limitation, the tamper resistance devices 83 may be configured for mechanical activation when the access panel 80 is moved without the locking device 82 being unlocked and/or when the locking device 82 is in the locked position. As another example, without limitation, the tamper resistance devices 83 may be electronically activated when authentication, such as at the authentication device 86, is attempted but fails a predetermined number of time (e.g., three failed attempts in a row). As yet another example, without limitation, the tamper resistance devices 83 may be remotely activated electronically, such as by way of the network communication devices 87. As yet another example, without limitation, the tamper resistance devices 83 may be activated when the drone 72 reports a location off course, delivery failure, errors, and/or a final location away from an assigned delivery location by more than a predetermined distance. One or more of these examples may be used separately or together and are provided by way of example and are not intended to be limiting.

The tamper resistance devices 83 may comprise one or more shredders. The shredders may be configured to mechanically shred one or more types of materials, such as but not limited to, paper, plastics, metals, combinations thereof, or the like. For example, without limitation, the shredders may be configured to mechanically shred contents of the compartment 76, such as the prescription container 78, medications therein, papers therein, combinations thereof, or the like. Alternatively, or additionally, the tamper resistance devices 83 may comprise a multipart resin. The tamper resistance devices 83 may be configured to selectively flood the compartment 76 with the multipart resin, which may be configured to harden (e.g., form a solid polymeric material) upon contact, thereby encasing the prescription container 78 or other items within the compartment 76. The tamper resistance devices 83 may be located within, or connected to, the compartment 76 in exemplary embodiments. Tamper resistance devices 83 of various kind may be utilized.

The tamper resistance devices 83 may, alternatively or additionally, comprise one or more lights, speakers, sirens, combinations thereof, or the like which may be activated when tampering is detected. The lights, speakers, sirens, combinations thereof, or the like may be located at an exterior portion of the container 74, so as to be seen and/or heard by others, for example, without limitation.

Upon detection of such tampering, the controllers 84 may be configured to generate and/or transmit one or more electronic notifications, such as by way of the network communication device 87 to the patient prescription databases subsystem 12, or components thereof, and/or to one or more remote devices, such as those associated with one or more law enforcement agencies and/or system administrators, for example, without limitation.

The tamper resistance devices 83 may, alternatively or additionally, comprise one or more cameras configured to capture images and/or videos upon detection or such tampering for local storage and/or transmission to one or more remote devices. The speakers, lights, and/or other components of the container 74 may be configured to indicate that the person(s) attempting to access the container are being recorded and/or authorities are being contacted, by way of non-limiting example.

Figure 6:
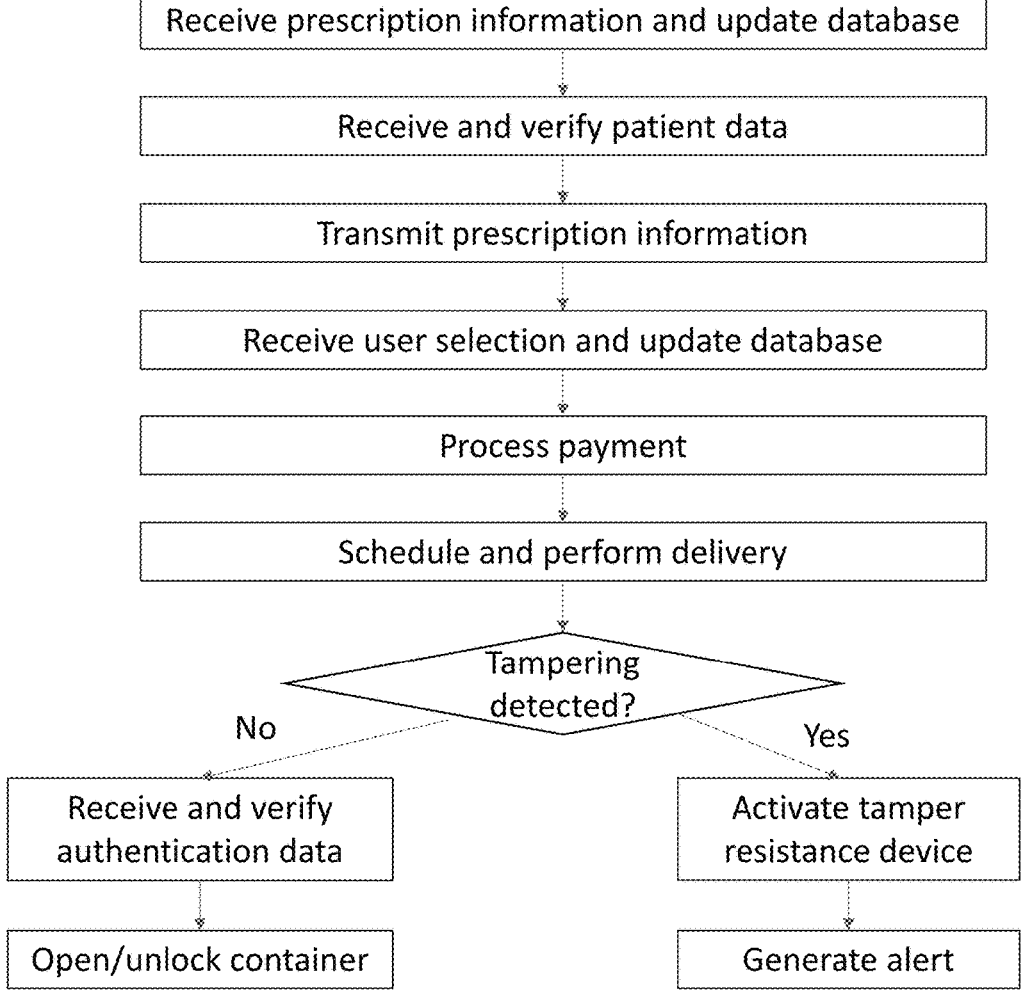
FIG. 6 is a flow chart with exemplary logic for operating the systems of FIGS. 1-5 and 7.

The system 10 may be utilized in accordance FIG. 6 by way of non-limiting example. Prescription information may be received at the patient prescription database subsystem 12, which may be updated accordingly. The prescription information may include, for example without limitation, newly prescribed medications, available refills, prescription expiration information, dosing information, patient information, supporting evidence, healthcare provider information, dispensing or preferred pharmacy information, combinations thereof, or the like. The prescription information may be received from the pharmacy system 16, the patient systems 18, and/or the healthcare provider system 20.

Patient data may be received and verified. Patient data may include, for example without limitation, name, address, social security number (full or partial), identification number, unique identifier, user name and/or password, PIN, keycode, one time access codes, passport numbers, authentication information (e.g., biometric information received by way of the authentication devices 22) combinations thereof, or the like. Such information may be verified at the patient prescription database subsystem 12. For example, without limitation, the patient data may be transmitted to the patient prescription database subsystem 12 for comparison against stored information.

Similar information may be stored at the patient prescription database subsystem 12 for healthcare providers and/or pharmacists. Similar information may be provided and verified for healthcare provider and/or pharmacist access, such as to enter new prescriptions, modify prescriptions, authorize refills, indicate dispensing of medications, combinations thereof, or the like. In exemplary embodiments, without limitation, such provision and verification of patient data may be performed when a healthcare provider, pharmacy personnel, and/or patient desires access to the patient prescription database subsystem 12 from the pharmacy system 16, the patient systems 18, and/or the healthcare provider system 20.

Prescription information may be retrieved and transmitted to the accessing, authenticated one or ones of the pharmacy system 16, the patient systems 18, and/or the healthcare provider system 20. The prescription information may include, for example without limitation, available prescriptions, medication information, prescriber information, dispensing pharmacy information, refill information, dosage information, expiration information, patient information, combinations thereof, or the like.

A user selection of one of the retrieved and transmitted prescriptions may be received at the patient prescription database subsystem 12, such as from the accessing, authenticated one or ones of the pharmacy system 16, the patient systems 18, and/or the healthcare provider system 20. The user selection may include a prescription in need or dispensing and/or refill, amount needed, location need at, payment information, delivery information, reason for need information, supporting evidence, combinations thereof, or the like. The patient prescription database subsystem 12 may be updated accordingly, such as to reflect the dispensing of the medication.

As needed, delivery or other pickup options may be scheduled and performed. Options may be displayed to user such as, but not limited to, by way of the user interface 54 and/or availability module 26. Delivery may be performed, for example without limitation, by way of the autonomous delivery subsystem 70.

Where the autonomous delivery subsystem 70 is used, the containers 74 may comprise one or more network communication devices 87 configured to transmit information to/from the patient prescription database subsystem 12 or components thereof. For example, without limitation, the network communication devices 87 may be utilized to transmit or receive authentication information to and/or from the authentication devices 86 to the patient prescription database subsystem 12 for verification. Alternatively, or additionally, the controllers 84 or other component of the container 74 may be electronically loaded with patient data for the patient for medication provided with the container 74, such as prior to deployment for local verification at the container 74. This may eliminate the need for wireless transmission of information, improving privacy and security eliminating many complexities, and/or expanding range of use, by way of non-limiting example.

Upon receipt of the container 74, the user may provide authentication information (e.g., biometrics, user name and passwords, one time access code information, keycode information, combinations thereof, or the like) which may be verified. Upon verification, the locking mechanism 82 may be placed in the unlocked position and/or the access panel 80 may be opened to permit access to the item(s) in the compartment(s) 76.

The patient prescription database subsystem 12 may be updated to reflect dispensation. Such updates may be performed automatically upon receipt of the user selection, payment confirmation (at the payment module 46 or otherwise), transmission of commands or other data to the delivery subsystem 70, receipt of data from the pharmacy system 16 indicating dispensation, receipt of data from the delivery subsystem 70 indicating departure or return of the containers 74 and/or drones 72, verification of the authentication information, combinations thereof, or the like. The patient prescription database subsystem 12 may be configured to automatically generate alerts where one or more of these items is missing, which may indicate theft, mis-delivery, combinations thereof, or the like.

The drones 72 and/or containers 74 may be equipped with location or other status tracking devices such that location of the drones 72 and/or containers 74 may be continuously, regularly, and/or periodically monitored, such as to confirm completion of delivery. For example, without limitation, the controller 84 may be configured to electronically record time and date information regarding successful authentication and/or store related authentication data received. Alternatively, or additionally, other evidence of delivery may be captured by the drones 72 and/or containers 74, such as one or more images by way of one or more cameras mounted to the same, electronic signature, combinations thereof, or the like.

Delivery may be provided to the patient, to a pharmacy, to a healthcare provider, and/or trusted third-party. This may be utilized to provider delivery to the patient of needed medications, to a pharmacy which may then dispense to one or more patients, and/or to healthcare provider for administration to one or more patients, by way of non-limiting example. In this manner, delivery may originate at a pharmacy, a warehouse, healthcare provider, combinations thereof, or the like and may terminate at a patient's residence or other location, pharmacy, healthcare provider office, combinations thereof, or the like. Any delivery origin or destination may be utilized.

A delivery location may be specified by the requesting party and/or provided automatically based on preprogrammed information and/or a detected location of a requesting device (e.g., the pharmacy system 16, the patient systems 18, and/or the healthcare provider system 20). For example, the pharmacy 60 location or patient residence may be pre-programmed. As another example, the patient system 18 may comprise one or more location service options which are configured to automatically detect and provide location information. Alternatively, location information may be specified, such as at one or more graphical user interfaces presented. Alternatively, or additionally, the targets 68 may be utilized to specify a more precise delivery location.

If tampering is detected, such as at any point during the delivery before authentication data is successfully received and verified, the tamper resistance devices 83 may be activated. If tampering is detected, the container 74 may be configured to, alternatively or additionally, generate one or more electronic notifications. For example, without limitation, the controllers 84 may generate a notification which is transmitted to the patient prescription database subsystem 12 and/or law enforcement by way of the network communication devices 87. If no such tampering is detected and the authentication data is successfully received and verified, the container 74 may be unlocked and/or opened.

Figure 7:
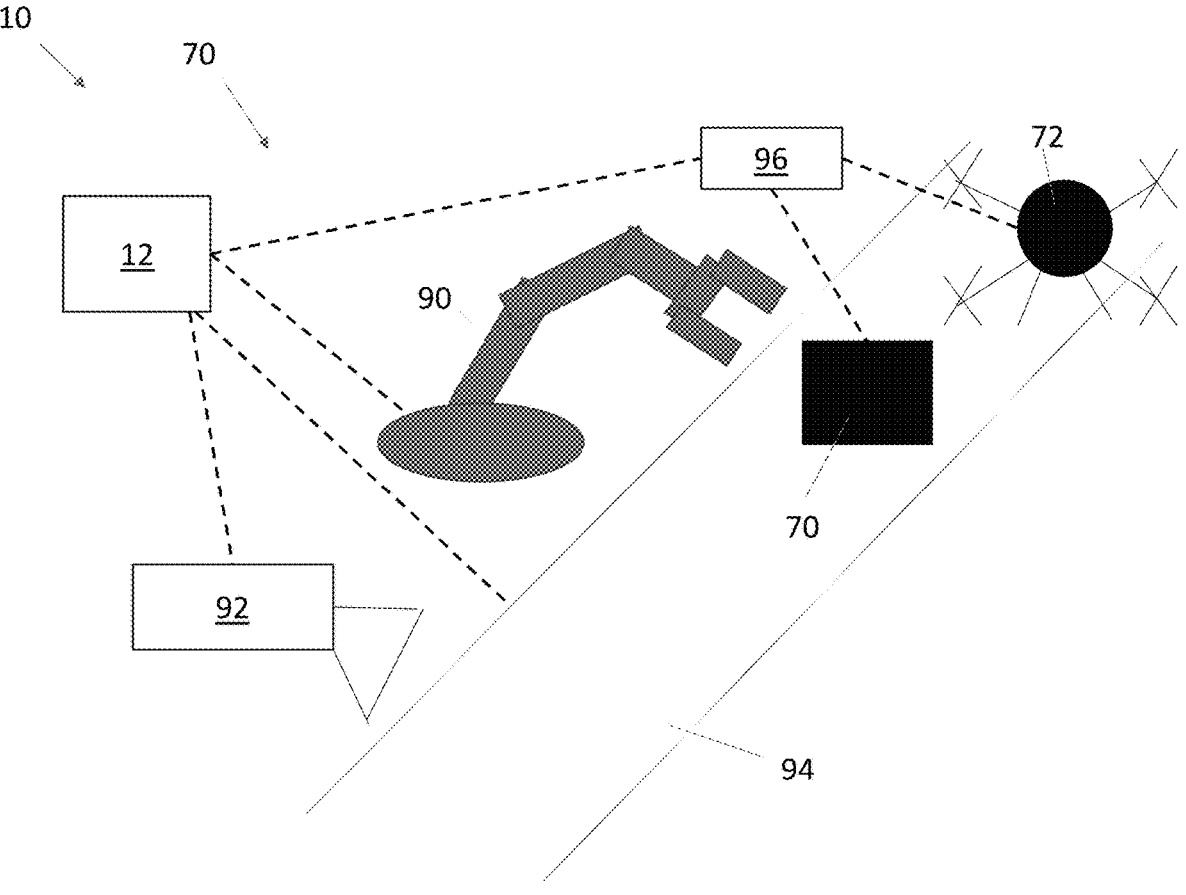
FIG. 7 is a plan view of other exemplary parts of the autonomous delivery subsystem for use with the system of FIG. 1.

As illustrated in FIG. 7, the containers 74 may be automatically assembled, loaded, and/or programmed (e.g., with medications, medication containers, programmed with authentication information, delivery information, combination thereof, or the like) by one or more robots 90 in an at least partially automated fashion, through such is not required. The containers 74 may be automatically secured to the drone 72 by one or more robots 90 or a same or different type in an at least partially automated fashion, through such is not required. Such robots 90 may comprise those available from FAUNC America Corp. of Rochester Hills, MI (www-.fanucamerica.com/products/robots/) by way of non-limiting example.

The autonomous delivery subsystem 70 may comprise one or more medication dispensers 92, programming devices 96, and/or conveyors 94, some or all of which may be fully or partially automated. The one or more medication dispensers 92, programming devices 96, and/or conveyors 94 may be controlled by the patient prescription database subsystem 12 and/or a separate controller.

The programming device(s) 96 may be configured to, by wired or wireless connection, program or reprogram the containers 70 with authentication or other information, and/or the drones 72 with delivery or other information, by way of non-limiting example. Upon return of the drones 72 and/or containers 70, the programming device(s) 96 may be configured to receive or upload data from the drones 72 and/or containers 70, such as but not limited to, authentication data, evidence of delivery, travel information, combinations thereof, or the like.

The conveyors 94 may comprise one or more belts or material handling devices. The conveyors 94 may be configured to move or otherwise manipulate the drones 72, the containers 70, and/or the medications or related prescription containers.

The medication dispensers 92 may comprise pill counters, container handlers, mixing machines, compounding machines, labeling machines, printers, combinations thereof, or the like. The medication dispensers 92 may be configured to automatically dispense an amount of medication, such as into a prescription container.

The system 10 may include some or all technology shown and/or described in US Pub. No. 2021/0358605 A1 published Nov. 18, 2021, the disclosures of which are hereby incorporated by reference as if fully restated herein.

Figures 8, 8B:
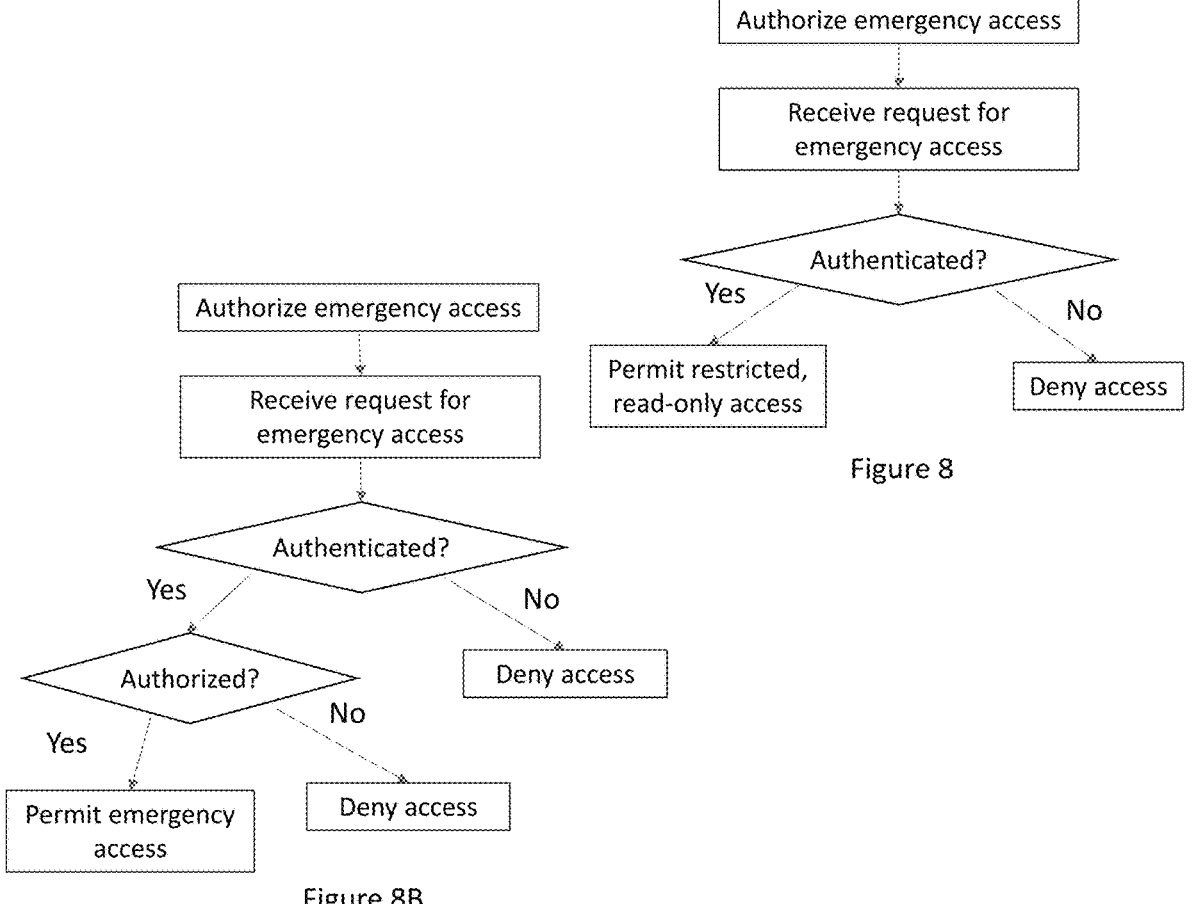
FIG. 8 is a flow chart with exemplary logic for operating the system of FIG. 1 under emergency access.
FIG. 8B is a flow chart with other exemplary logic for operating the system of FIG. 1 under emergency access.

In exemplary embodiments, without limitation, the system 10, or certain components thereof, may be operated under emergency procedures and/or an emergency access mode in certain circumstances such as illustrated in FIG. 8.

Users may opt in to emergency access authorization, for example without limitation. Such opt in may be selected at registration or later. In other exemplary embodiments, users may be required to opt-out of emergency access authorization. Such opt-in and/or opt-out may be stored at the patient prescription database subsystem 12 such as indicated by way of user selections at the user patient systems 18, by way of non-limiting example.

A request for emergency access may be received, such as at the patient prescription database subsystem 12. The emergency access request may be received at one of the healthcare provider systems 20, such as may be associated with emergency caregiver personnel (e.g., EMT, paramedic, first responder, police, law enforcement, security, emergency room providers, combinations thereof of the like) by way of non-limiting example. For example, without limitation, one of the healthcare provider system 20 may be associated with a first responder who finds an unconscious patient at an accident scene with photo ID in their wallet or identified by another individual at the scene, for example. Regardless, authentication may be performed at the healthcare provider systems 20 by way of the authentication device(s) 22 to authenticate the emergency provider. Upon successful authentication, the provider, by way the healthcare provider systems 20 may request emergency access to any medical data stored at the patient prescription database subsystem 12 associated with the patient. For example, without limitation, the healthcare provider may provide name information for the patient, such as by way of the one of the healthcare provider system 20. The patient prescription database subsystem 12, may be configured to permit read-only access to such medical data. For example, without limitation, the patient prescription database subsystem 12 may automatically query for any data stored matching the provided patient information and provide the data on a read-only basis. In this fashion, certain medical information such as prescribed medications, recently dispensed medications, medical history information, patient information, allergy information, recent travel information, combinations thereof, or the like may be provided on an emergency basis.

In exemplary embodiments, the patient prescription database subsystem 12 may be configured to provide the patient data in an encrypted and/or time dependent manner such that it automatically deletes, expires, or the like after a predetermined period of time, such as 1 or 24 hours, though any amount of time may be utilized. This may reduce the potential for unauthorized access or copying.

Alternatively, or additionally, the patient prescription database subsystem 12 may be configured to generate a one-time access code ("OTAC") which is configured to be accepted by the one of the patient systems 20 associated with the patient identified by the emergency provider. In this fashion, the device of the patient may be accessed to likewise access the medical data stored thereon. This may reduce fraud as the matching one of the patient systems 20 would be required to access the data.

Alternatively, or additionally, the patient prescription database subsystem 12 may be configured to remotely unlock the one of the patient systems 20 associated with the patient identified by the emergency provider, such as by remotely transmitted electronic signal(s). This may reduce fraud as the matching one of the patient systems 20 would be required to access the data.

FIG. 8B illustrates another exemplary emergency access procedure. In exemplary embodiments, without limitation, authentication may be performed at the healthcare provider system(s) 20 by way of the authentication device(s) 22 to authenticate the patient. For example, without limitation, the patient's fingers or other biometric information may be provided at the authentication device(s) 22 of the healthcare provider system(s) 20 associated with the emergency provider(s). To provide a more specific scenario, by way of non-limiting example, an unconscious patient's fingers may be manipulated by a first responded to place them on a smartphone. The patient prescription database subsystem 12 may be configured to verify the authentication information for the patient and confirm that the patient has authorized emergency access. If successfully authenticated and indicated as authorized, the patient prescription database subsystem 12 may retrieve and/or transmit some or all of the available data for the patient to the healthcare provider system(s) 20 associated with the emergency provider(s). Retrieval of the information may be performed concurrent with, or after, authentication and authorization verification. In exemplary embodiments, without limitation, the retrieved and/or transmitted information may be provided in a read-only format, be limited to active or recent information (e.g., within a pre-determined lookback period), combinations thereof, or the like. This may permit access even where patient identity is unknown, and may provide identification information for the patient.

The patient prescription database subsystem 12 may comprise emergency contact information and/or next of kin information for at least some of the patients. The patient prescription database subsystem 12 may be configured to automatically notify any provided emergency contacts or next of kin upon emergency access to the data for a given patient. Alternatively, or additionally, the emergency contact information and/or next of kin information may be provided to the requesting healthcare provider device(s) 20.

FIG. 9 illustrates an exemplary medication information features of the system 10. In exemplary embodiments, without limitation, information for prescriptions registered to users may be automatically uploaded, such as but not limited to, by way of the one or more medication information databases 32. Alternatively, or additionally, the information may be manually entered or updated. The information may include, for example without limitation, names, images, or descriptions of the medications, diseases, disorders, or the like commonly associated with the medications, known side effects, status of prescription (recently filled, currently taking, taken within the past month, etc.), prescribing provider, dispensing pharmacy, combinations thereof, of the like. Any type or kind of information may be provided.

The information may be presented in one or more graphical user interfaces ("GUIs") 34, such as shown in FIG. 10 by way of non-limiting example. In this fashion, emergency providers may be quickly provided with information about the patient. The GUI(s) 34 may be displayed at the patient systems 18, healthcare provider systems 20, and/or pharmacy systems 16 by way of example without limitation. For example, without limitation, while sometimes discussed with regard to an emergency provider, the medication information and related GUI(s) 34 may be provided to any user, such as but not limited to, the patient, healthcare provider, pharmacist, combinations thereof, or the like. The type, arrangement, and content of the information illustrated is merely exemplary and not intended to be limiting. For example, without limitation, selecting (by touch or otherwise) a particular one of the displayed prescriptions may cause additional information or options to be displayed.

FIG. 11 illustrates an exemplary medication identification features of the system 10. In exemplary embodiments, without limitation, information for prescriptions registered to users may be automatically uploaded, such as but not limited to, by way of the one or more medication information databases 32. The information may include, for example without limitation, images and/or description information regarding prescribed medications so that a user may more easily identify the medication. Optionally, images and/or description information may be uploaded by users. Users may include, by way of example and without limitation, patients, healthcare providers, and/or pharmacists. The images and/or other information may be displayed at the patient systems 18, healthcare provider systems 20, and/or pharmacy systems 16 by way of example without limitation, such as at one or more GUIs 36 such as shown in FIG. 12 by way of example, without limitation. The type, arrangement, and content of the information illustrated is merely exemplary and not intended to be limiting. For example, without limitation, selecting (by touch or otherwise) a particular one of the displayed prescriptions may cause additional information or options to be displayed.

Figure 13:
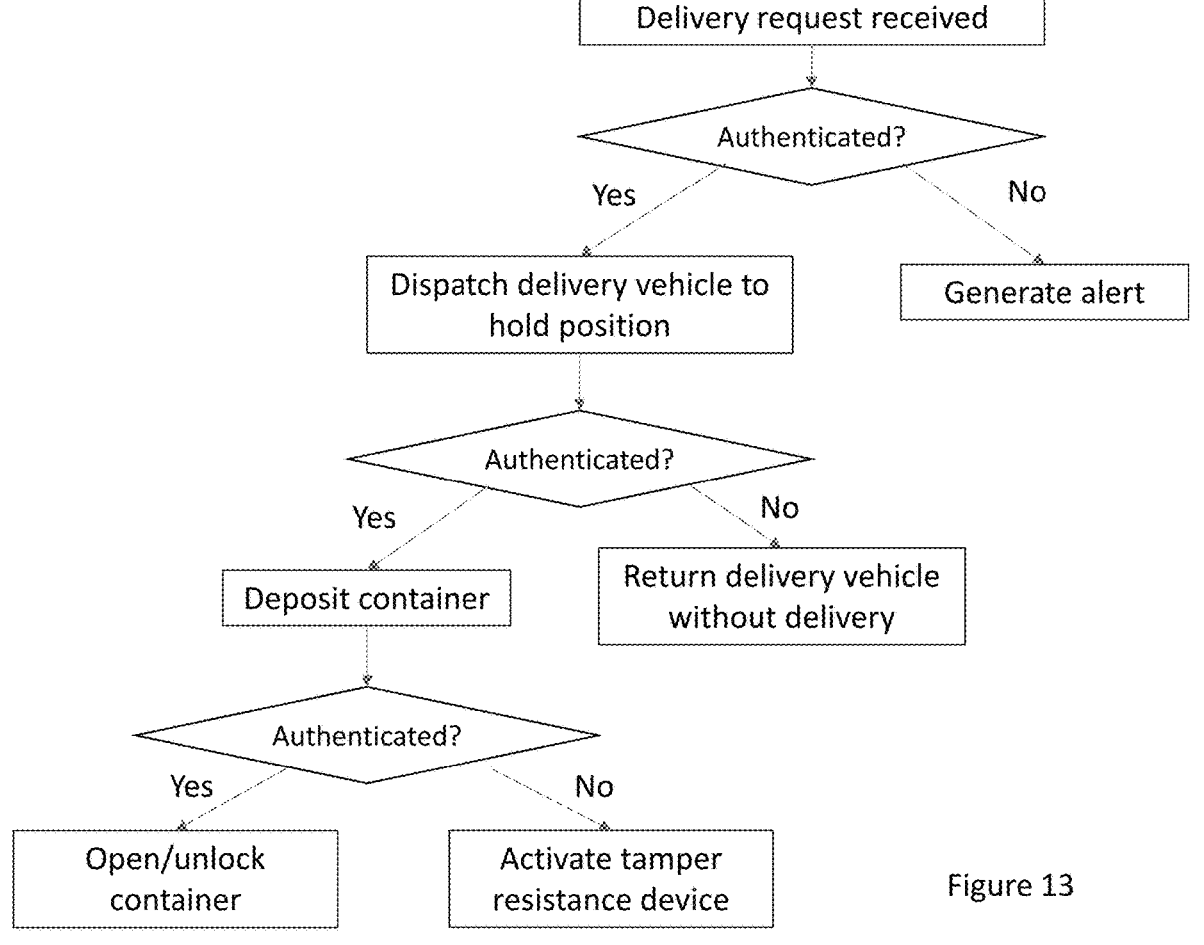
FIG. 13 flow chart with exemplary logic for operating the systems of at least FIGS. 1-7.

FIG. 13 illustrates exemplary logic for operating the system 10, such as for fully or partially autonomous delivery, such as with the delivery subsystem 70. Once a request for prescription delivery is received, and/or payment is received, such as at the patient prescription database subsystem 12, the delivery may be prepared, such as with the delivery subsystem 70. Some or all of the preparation of the delivery and/or dispatch of the done 72 may be withheld until authentication information is received and verified, such as at the patient prescription database subsystem 12 from a patient system 18 and/or authentication device 22.

If such information is not received and/or not verified, an alert may be generated. The alert may be provided to the recipient (e.g., denying request, requesting reattempt at authentication) and/or may trigger flagging or removing the user at the patient prescription database subsystem 12, such as for suspected fraud.

If the authentication information is received and verified, the drone 72 may be dispatched. The drone 72 may be dispatched to a location manually inputted and/or automatically determined and transmitted from the patient system 18, as specified by the user (e.g., in delivery request from patient, healthcare provider, and/or pharmacist, by way of non-limiting example), combinations thereof, or the like. For example, without limitation, the drone 72 may be automatically programmed to travel towards the user's location, such as automatically detected by the patient system 18.

The drone 72 may be configured to remain at a nearby location until authentication is received and verified a second time, such as at the patient prescription database subsystem 12 from a patient system 18 and/or authentication device 22. The authentication information does not necessarily need to be the same and/or received from the same devices. For example, without limitation, a healthcare provider or pharmacist may request the prescription delivery. Initial, first round of authentication may be of the healthcare provider and/or pharmacist and received from the respective systems 20, 16 and/or authentication device(s) 22. The further, second round of authentication may be from the patient, such as received from the patient system 18 and/or authentication device 22.

The nearby location may be within a predetermined distance of the delivery location in exemplary embodiments. For example, without limitation, the drone 72 may be configured to hover at a predetermined height (e.g., 100 feet, 50 feet, etc.) above the location, stay a predetermined distance (e.g., 75 feet, 150 feet, etc.) from the location, circle the location, combinations thereof, or the like. If such authentication information is not received and/or verified, such as within a predetermined amount of time (e.g., 5 minutes, 10 minutes, etc.) or after a predetermined number of attempts (e.g., 2 attempts, three attempts, etc.) the drone 72 may be configured to automatically return to its origin or another location and/or alert(s) may be generated. If such authentication information is received and verified, the drone 72 may be configured to proceed to the location and deposit the container 74.

The container 74 may then operate as shown and/or described with regard to FIG. 6 by way of non-limiting example. In exemplary embodiments, without limitation, the container 74 may only be opened and/or unlocked upon receipt and verification of the authentication information, such as at the patient prescription database subsystem 12 from the patient system 18 and/or authentication device 22, for a third time. The third, final round of authentication information may be successful only upon receipt and verification of the patient data. If not so received and/or verified, and/or if tampering is detected, the tamper resistance device(s) 83 may be activated and/or alert(s) may be generated. In other exemplary embodiments, without limitation, all three rounds of authentication information may be received from the patient system 18 and/or authentication device 22 for the patient.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers or specialized computing devices. The electronic devices may be personal computers, smartphone, tablets, databases, servers, or the like. The electronic connections described herein may be accomplished by wired or wireless means. The computerized hardware, software, components, systems, steps, methods, and/or processes described herein may serve to improve the speed of the computerized hardware, software, systems, steps, methods, and/or processes described herein. The electronic devices, including but not necessarily limited to the electronic storage devices, databases, or the like, may comprise and/or be configured to hold, solely non-transitory signals.

What is claimed is:

1. A system for providing emergency access to information regarding prescribed medications, said system comprising:

healthcare provider devices, at least some of which are associated with emergency providers, and each of which are associated with at least one authentication device;

patient devices, each of which are associated with at least one authentication device and a patient;

a patient prescription database subsystem comprising one or more servers and one or more databases comprising prescription information and authentication information associated with patient data for the patients, where at least some of said patient data is associated with authorization for emergency access, said one or more servers comprising software instructions, which when executed, configure said one or more servers to:

receive a request for emergency access from a requesting one of said healthcare provider devices associated with one of said emergency providers, said request for emergency access comprising authentication information for one of said patients received from the at least one authentication device associated with the requesting healthcare provider device;

verify said authentication information for said patient;

determine if said patient data for said patient includes an authorization for emergency access, and if so:

query said one or more databases to retrieve said prescription information associated with said patient data for said patient; and transmit said prescription information retrieved from said one or more databases to said requesting healthcare provider device in a read-only format.

2. The system of claim 1 wherein:

said authentication information comprises biometric information; and said at least one authentication device associated with said healthcare provider devices is configured to collect said biometric information.

3. The system of claim 2 wherein:

said biometric information comprise at least one fingerprint; and said at least one authentication device associated with said healthcare provider devices comprises a fingerprint reader.

4. The system of claim 1 wherein:

said one or more servers comprise additional software instructions, which when executed, configure said one or more servers to:

receive, as part of said request for emergency access from said requesting one of said healthcare provider devices associated with said one of said emergency providers, authentication information for one of said healthcare providers received from the at least one authentication device associated with the requesting healthcare provider device;

verify said authentication information for said healthcare provider prior to querying said one or more databases to retrieve said prescription information associated with said patient data for said patient.

5. The system of claim 1 wherein:

said healthcare provider devices comprise smartphones; and said patient devices comprise smartphones.

6. The system of claim 1 wherein:

said one or more servers comprise additional software instructions, which when executed, configure said one or more servers to:

deny access where said authentication information for said patient is not successfully verified; and deny access where said patient data for said patient does not include the authorization for emergency access.

7. The system of claim 1 wherein:

said one or more servers comprise additional software instructions, which when executed, configure said one or more servers to:

query said one or more databases to retrieve said prescription information associated with said patient data for said patient over a predetermined lookback period.

8. The system of claim 1 wherein:

said prescription information comprises a list of medications taken by each of the patients and patient-specific information for each of said medications.

9. The system of claim 8 wherein: said patient-specific information comprises one of: side effect information, associated disease or disorder information, prescription status information, prescribing provider information, and dispensing pharmacy information.

10. The system of claim 9 wherein: said patient-specific information comprises each of: side effect information, associated disease or disorder information, prescription status information, prescribing provider information, and dispensing pharmacy information.

11. The system of claim 1 wherein:

said prescription information comprises a list of medications taken by the patient and images and/or descriptions for each of said medications.

12. The system of claim 1 wherein:

said one or more databases comprising emergency contact information associated with said patient data for the patients; and said one or more servers comprise additional software instructions, which when executed, configure said one or more servers to:

where said authentication information for said patient is successfully verified and said patient data for said patient includes said authorization for emergency access, query said one or more databases to retrieve said emergency contact information for said patient.

13. The system of claim 1 wherein:

said one or more servers comprise additional software instructions, which when executed, configure said one or more servers to:

after querying said one or more databases to retrieve said emergency contact information for said patient, cause an electronic notification to be automatically generated and provided to said emergency contact information.

14. The system of claim 1 wherein:

said one or more servers comprise additional software instructions, which when executed, configure said one or more servers to:

after querying said one or more databases to retrieve said emergency contact information for said patient, cause said emergency contact information to be provided to said requesting one of said healthcare provider devices.

15. A system for providing emergency access to information regarding prescribed medications, said system comprising:

healthcare provider devices, at least some of which are associated with emergency providers, and each of which are associated with at least one authentication device configured to collect biometric information;

patient devices, each associated with a patient;

a patient prescription database subsystem comprising one or more servers and one or more databases comprising biometric information associated with patient data for the patients and prescription information comprising a list of mediations taken by each of the patients and patient-specific information for each of said medications, where at least some of said patient data is associated with preauthorization for emergency access, said one or more servers comprising software instructions, which when executed, configure said one or more servers to:

receive a request for emergency access from a requesting one of said healthcare provider devices associated with one of said emergency providers, said request for emergency access comprising authentication information for one of said patients received from the at least one authentication device associated with the requesting healthcare provider device;

verify said authentication information for said patient;

following successful verification of said authentication information, determine if said patient data for said patient includes the preauthorization for emergency access, and if so:

query said one or more databases to retrieve said prescription information associated with said patient data for said patient; and transmit said prescription information retrieved from said one or more databases to said requesting healthcare provider device in a read-only format;

deny access where said authentication information for said patient is not successfully verified; and deny access where said patient data for said patient does not include the preauthorization for emergency access.

16. The system of claim 15 wherein:

said one or more servers comprise additional software instructions, which when executed, configure said one or more servers to:

query said one or more databases to retrieve said prescription information associated with said patient data for said patient over a predetermined lookback period.

17. The system of claim 15 wherein:

said patient-specific information comprises one or more of: side effect information, associated disease or disorder information, prescription status information, prescribing provider information, and dispensing pharmacy information.

18. The system of claim 15 wherein:

said prescription information comprises a list of mediations taken by the patient and images and/or descriptions for each of said medications.

19. The system of claim 15 wherein:

said one or more databases comprising emergency contact information associated with said patient data for the patients; and said one or more servers comprise additional software instructions, which when executed, configure said one or more servers to:

where said authentication information for said patient is successfully verified and said patient data for said patient includes said preauthorization for emergency access, query said one or more databases to retrieve said emergency contact information for said patient; and after querying said one or more databases to retrieve said emergency contact information for said patient, at least one of:

cause an electronic notification to be automatically generated and provided to said emergency contact information; and cause said emergency contact information to be provided to said requesting one of said healthcare provider devices.

20. A system for providing emergency access to information regarding prescribed medications, said system comprising:

healthcare provider devices, at least some of which are associated with emergency providers, and each of which are associated with at least one authentication device;

patient devices, each of which is associated with a patient;

a patient prescription database subsystem comprising one or more servers and one or more databases comprising prescription information and authentication information associated with patient data for the patients, where at least some of said patient data is associated with a preauthorization for emergency access, said one or more servers comprising software instructions, which when executed, configure said one or more servers to:

receive a request for emergency access from a requesting one of said healthcare provider devices associated with one of said emergency providers, said request for emergency access comprising authentication information for one of said patients and one of said healthcare providers received from the at least one authentication device associated with the requesting healthcare provider device;

verify said authentication information for said patient and said healthcare provider;

following successful verification of said authentication information, determine if said patient data for said patient includes the preauthorization for emergency access, and if so:

query said one or more databases to retrieve said prescription information associated with said patient data for said patient; and transmit said prescription information retrieved from said one or more databases to said requesting healthcare provider device in a read-only format.

\* \* \* \* \*